United States Patent
Xiong et al.

(10) Patent No.: US 12,385,006 B2
(45) Date of Patent: Aug. 12, 2025

(54) *ZAVARZINIA COMPRANSORIS* CAPABLE OF DEGRADING ORGANOPHOSPHORUS FLAME RETARDANT AND USE THEREOF

(71) Applicant: GUANGDONG UNIVERSITY OF TECHNOLOGY, Guangdong (CN)

(72) Inventors: Jukun Xiong, Guangdong (CN); Yongyu Liang, Guangdong (CN); Yi Guo, Guangdong (CN); Guiying Li, Guangdong (CN); Taicheng An, Guangdong (CN)

(73) Assignee: GUANGDONG UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 18/721,879

(22) PCT Filed: Nov. 14, 2022

(86) PCT No.: PCT/CN2022/131638
§ 371 (c)(1),
(2) Date: Jun. 20, 2024

(87) PCT Pub. No.: WO2024/087263
PCT Pub. Date: May 2, 2024

(65) Prior Publication Data
US 2025/0051716 A1    Feb. 13, 2025

(30) Foreign Application Priority Data

Oct. 26, 2022   (CN) .......................... 202211319602.4

(51) Int. Cl.
| | | |
|---|---|---|
| *C12N 1/20* | (2006.01) | |
| *B09C 1/10* | (2006.01) | |
| *C02F 3/34* | (2023.01) | |
| *C02F 101/36* | (2006.01) | |
| *C12R 1/01* | (2006.01) | |

(52) U.S. Cl.
CPC ................ *C12N 1/205* (2021.05); *C02F 3/34* (2013.01); *B09C 1/10* (2013.01); *C02F 2101/36* (2013.01); *C12R 2001/01* (2021.05)

(58) Field of Classification Search
CPC ... C12N 1/205; C12N 1/20; C02F 3/34; C02F 2101/36; C02F 2101/30; B09C 1/10; C12R 2001/01; A62D 3/02; C09K 17/14
See application file for complete search history.

(56) References Cited

U.S. PATENT DOCUMENTS

2011/0296747 A1   12/2011   Sonomoto et al.

FOREIGN PATENT DOCUMENTS

| CN | 102154174 | 8/2011 |
|---|---|---|
| CN | 104261568 | 1/2015 |
| CN | 105530954 | 4/2016 |
| CN | 106006993 | 10/2016 |
| CN | 109609397 | 4/2019 |
| CN | 113897314 | 1/2022 |

OTHER PUBLICATIONS

"International Search Report (Form PCT/ISA/210) of PCT/CN2022/131638", mailed on Jun. 20, 2023, with English translation thereof, pp. 1-5.

*Primary Examiner* — Iqbal H Chowdhury
(74) *Attorney, Agent, or Firm* — JCIPRNET

(57) ABSTRACT

*Zavarzinia compransoris* capable of degrading an organophosphorus flame retardant and a use of *Zavarzinia compransoris*. A GDUTXIONG2 strain of *Zavarzinia compransoris* capable of degrading an organophosphorus flame retardant is obtained by research, the strain is preserved in China Center for Type Culture Collection (CCTCC) on 10 Jun. 2022, and the accession number is CCTCC NO: M2022855. The GDUTXIONG2 strain has an excellent degradation ability to an organophosphorus flame retardant, the rate of degradation on an organophosphorus flame retardant, i.e., Tris(1,3-dichloroisopropyl)phosphate (TDCPP) can reach more than 99.9%, and the GDUTXIONG2 strain is an efficient degrading bacterium. The GDUTXIONG2 strain can be used for preparing a degrading bacterial agent, is pollution-free and nuisance-free during use, and can be better used for used for the remediation and treatment of the environment polluted by organophosphorus flame retardants.

9 Claims, 4 Drawing Sheets
Specification includes a Sequence Listing.

FIG. 3

SEQUENCE LISTING

```
Sequence total quantity: 3
SEQ ID NO: 1            moltype = DNA   length = 18
FEATURE                 Location/Qualifiers
source                  1..18
                        mol_type = other DNA
                        organism = synthetic construct
SEQUENCE: 1
cagagtttga tcctggct                                                   18

SEQ ID NO: 2            moltype = DNA   length = 19
FEATURE                 Location/Qualifiers
source                  1..19
                        mol_type = other DNA
                        organism = synthetic construct
SEQUENCE: 2
aggaggtgat ccagccgca                                                  19

SEQ ID NO: 3            moltype = DNA   length = 1348
FEATURE                 Location/Qualifiers
source                  1..1348
                        mol_type = genomic DNA
                        organism = Zavarzinia compransoris
SEQUENCE: 3
tcttcggatg gcgtggcgga cgggtgagta acacgtggga acctgcccag aggtacggga    60
taacccaggg aaacttggga caataccgta tgtgacctga gggtgaaaga tttatcgcct   120
ttggatgggc ccgcgtcgga ttaggtagtt ggtggggtaa aggcctacca agccgacgat   180
ccgtagctgg tctgagagga tgatcagcca cactgggact gagacacggc ccagactcct   240
acgggaggca gcagtgggga atattggaca atgggcgcaa gcctgatcca gcaatgccgc   300
gtgagtgatg aaggccttag ggttgtaaag ctctttcacc cacgacgatg atgacggtag   360
tgggagaaga agccccggct aacttcgtgc cagcagccgc ggtaatacga aggggggctag   420
cgttgttcgg aatgactggg cgtaaagggc gcgtaggcgg ttgaccaagt tgggggtgaa   480
agcccgggc ttaacctcgg aattgcctcc aaaactggtc ggcttgagtg tggaagaggg   540
ttgtggaatt cccagtgtag aggtgaaatt cgtagatatt gggaagaaca ccagtggcga   600
aggcgacaac ctggtccatt actgacgctg aggcgcgaca gcgtggggag caaacaggat   660
tagataccct ggtagtccac gccgtaaacg atgagtgctg gatgttggac ggttgccgtt   720
cagtgtcgaa gttaacgcga taagcactcc gcctggggag tacggccgca aggttgaaac   780
tcaaaggaat tgacggggc ccgcacaagc ggtggagcat gtggtttaat tcgaagcaac   840
gcgcagaacc ttaccaaccc ttgacatggg aagtttgggc tcgagagatt gggtccttca   900
gttcggctgg cttccacaca ggtgctgcat ggctgtcgtc agctcgtgtc gtgagatgtt   960
gggttaagtc ccgcaacgag cgcaaccctc gcctttagtt gccatcattc agttgggcac  1020
tctaaaggaa ccgccggtga caagccgag gaaggtgggg atgacgtcaa gtcctcatgg  1080
cccttacggg ttgggctaca cacgtgctac aatggtggtg acagtgggtt gcgaggcagc  1140
gatgccaagc taatcccccaa aagccacctc agttcggatt gttctctgca actcgagagc  1200
atgaaggcgg aatcgctagt aatcgcggat cagcatgccg cggtgaatac gttcccgggc  1260
cttgtacaca ccgcccgtca caccatggga gttggttta cccgaagccg gtgcgctaac  1320
cgcaaggagg cagccgacca cggtaagg                                     1348
```

ZAVARZINIA COMPRANSORIS CAPABLE OF DEGRADING ORGANOPHOSPHORUS FLAME RETARDANT AND USE THEREOF

CROSS-REFERENCE TO RELATED APPLICATION

This is a 371 application of the International PCT application serial no. PCT/CN2022/131638, filed on Nov. 14, 2022, which claims the priority benefits of China Application No. 202211319602.4, filed on Oct. 26, 2022. The entirety of each of the above-mentioned patent applications is hereby incorporated by reference herein and made a part of this specification.

TECHNICAL FIELD

The present invention is in the technical field of microbial degradation. More particularly, it relates to a *Zavarzinia compransoris* capable of degrading organophosphorus flame retardants and use thereof.

DESCRIPTION OF RELATED ART

Organophosphorus flame retardants are a class of synthetic industrial organic additives, which are widely used in various commercial and industrial fields, such as electronic equipment, building materials, textiles, paints, and furniture. Organophosphorus flame retardants are mainly added to materials in physical form and enter the environment through volatilization, abrasion, and dissolution during use, resulting in the widespread presence of organophosphorus flame retardants in various media such as water, sediment, and soil. Toxicological studies have shown that organophosphorus flame retardants have teratogenic, carcinogenic, mutagenic, and neurotoxic effects, and even when exposed to low concentrations, long-term accumulation can cause potentially great harm to human health.

The biological method is a method for degrading organophosphorus flame retardants in the environment using the metabolic activity of microorganisms, which has the advantages of no secondary pollution, large treatment capacity, low operation cost, and good purification effect.

At present, few microbial strains can be used in the degradation of organophosphorus flame retardants by biological methods, and there are only reports in the prior art that *Bacillus thuringiensis* (Bt) can degrade tris (2-chloroethyl) phosphate; *Sphingomonas* sp. can degrade triphenyl phosphate; *Burkholderia* HQL1813 can degrade methylphosphonic acid efficiently; and mixed microbial flora (*Hyphomicrobiun*, *Chryseobacterium* and *Sphingopyxis*) has a degradation effect on the organophosphorus flame retardants triphenyl phosphate and tricresyl phosphate. So far, there are no more microbial research reports on other bacteria that can be used in the degradation of organophosphorus flame retardants. Therefore, in order to discover more organophosphorus flame retardant degradation bacteria with better degradation effects and apply them to the contaminated environment, it will effectively reduce the content of harmful pollution in the environment and provide more choices for the biological degradation of organophosphorus flame retardants.

SUMMARY

The technical problem to be solved by the present invention is to overcome the above-mentioned defects and deficiencies and provide a *Zavarzinia compransoris* capable of degrading organophosphorus flame retardants and use thereof.

It is an object of the present invention to provide a strain of *Zavarzinia compransoris*.

Still another object of the present invention is to provide a degrading microbial agent for organophosphorus flame retardants.

It is another object of the present invention to provide the use of the *Zavarzinia compransoris* GDUTXIONG2 strain.

Preferably, the *Zavarzinia compransoris* GDUTXIONG2 is used to degrade organophosphorus flame retardants in environments including water and soil.

Preferably, the organophosphorus flame retardant is tris (1,3-dichloropropyl) phosphate (TDCPP).

The above object of the present invention is achieved by the following technical solution:

In the present invention, a high-efficiency degradation bacterium capable of degrading organophosphorus flame retardants, *Zavarzinia compransoris* GDUTXIONG2 strain, has been deposited in China Center for Type Culture Collection on Jun. 10, 2022, with the accession number CCTCC NO: M 2022855, which is screened, isolated and purified from the sludge of a sewage treatment plant in Guangzhou, Guangdong Province. The GDUTXIONG2 strain is gram-negative, the colony morphology is round, off-white, and translucent, and has a colony diameter of 0.5~1.5 mm; of which the morphology is rod-shaped, and the size is 0.8-1.0×0.2-0.3 μm, without flagella; it grows in anaerobic conditions and it is positive for both oxidase and glucose OF utilization; and it is negative for gram stain, nitrate reduction, Simon's citrate utilization, hydrolyzed gelatin, arabinose, mannitol, and xylose utilization.

The present study showed that the GDUTXIONG2 strain could efficiently degrade organophosphorus flame retardants, and the degradation rate of 1-15 mg/L tris (1,3-dichloropropyl) phosphate could reach 99.9% in 96 h. It could be used for rapid degradation of TDCPP and could be used in the remediation and treatment of environments contaminated with organophosphorus flame retardants.

Accordingly, the present invention provides the uses of the *Zavarzinia compransoris* GDUTXIONG2 strain in the degradation of organophosphorus flame retardants, in the preparation of a degrading microbial agent for organophosphorus flame retardants, in the remediation of environments contaminated with organophosphorus flame retardants.

Preferably, the organophosphorus flame retardant is tris (1,3-dichloropropyl) phosphate (TDCPP).

The present invention provides a degrading microbial agent for organophosphorus flame retardants including the above-mentioned *Zavarzinia compransoris* GDUTXIONG2 strain and/or a bacterial liquid thereof.

Preferably, the concentration of the bacterial liquid is not less than 2.0×10⁶ CFU/mL.

The present invention provides a method for degrading organophosphorus flame retardants, which treats the organophosphorus flame retardant with the above-mentioned *Zavarzinia compransoris* GDUTXIONG2 strain and/or the bacterial liquid thereof.

Preferably, the inoculum size of the strain is 1%-10%.

Preferably, the treatment conditions are pH 6.5-7.5, temperature 30-40° C., and time 24-120 h.

More preferably, the treatment conditions are pH 7.3, temperature 37° C., and time 96 h.

The present invention has the following advantageous effects:

The present invention provides a *Zavarzinia compransoris* GDUTXIONG2 strain capable of degrading organophosphorus flame retardants, which has an excellent degradation ability to organophosphorus flame retardants, and the degradation rate of the organophosphorus flame retardant tris (1,3-dichloropropyl) phosphate can reach 99.9% or more and is a highly efficient degradation bacterium; at the same time, GDUTXIONG2 strain is pollution-free and nuisance-less in use, and can be used in the remediation and treatment of the environments contaminated with organophosphorus flame retardants. It has important practical significance and value for the degradation of organophosphorus flame retardants and remediation of the environments contaminated with organophosphorus flame retardants.

BRIEF DESCRIPTION OF THE DRAWINGS

FIG. 3 is a graph of the homology analysis of *Zavarzinia compransoris* GDUTXIONG2;

DESCRIPTION OF THE EMBODIMENTS

The invention will now be further described with reference to the accompanying drawings and specific examples, which are not intended to limit the invention in any way. Unless otherwise indicated, the reagents, methods, and equipment used herein are those conventional in the art.

Unless otherwise noted, the reagents and materials used in the following examples are commercially available.

The inorganic salt medium formula used in the following examples was: phosphate buffer solution: $K_2HPO_4 \cdot H_2O$ 1.75 g/L, $NaHPO_4 \cdot 12H_2O$ 3.40 g/L, $KH_2PO_4$ 1.5 g/L; $MgSO_4$ solution: $MgSO_4$ 1.5 g/L; $CaCl_2$ solution: 1.4 g/L; $FeCl_3$ solution: $FeCl_3 \cdot 6H_2O$ 0.25 g/L, $MnSO_4 \cdot H_2O$ 0.9 mg/L; microelement solution: $ZnSO_4 \cdot H_2O$ 0.8 mg/L, $(NH4)_6Mo_7O_{24} \cdot 4H_2O$ 0.7 mg/L.

The solid medium formula was beef extract 3.0 g/L, peptone 10.0 g/L, NaCl 5.0 g/L.

Example 1 Isolation of Strains

The sample was sludge from a sewage treatment plant in Guangzhou, Guangdong Province. Organophosphorus flame retardant (TDCPP) was used as a carbon source and energy source. Organophosphorus flame retardant was added into an inorganic salt medium for screening, with the acclimation substrate concentration of 1 mg/L, 5 mg/L, 10 mg/L, 15 mg/L and 20 mg/L. First, 10 mL sludge was taken and added into an inorganic salt medium containing 1 mg/L organophosphorus flame retardant. After acclimation at 37° C. for 5 days, the bacteria were transferred into the next concentration at 10% inoculum size and then acclimated, and then the concentration was gradually increased to acclimate.

At the end of acclimation, the final concentration of bacterial liquid was diluted by 10-1 to $10^{-7}$ times, and seven dilutions of $10^{-1}$, $10^{-2}$, $10^{-3}$, 10-4, $10^{-1}$, $10^{-6}$, and $10^{-7}$ were selected respectively, 0.2 mL of each dilution was taken and evenly spread in the solid medium with organophosphorus flame retardant as a carbon source for cultivation, and a single colony with good growth status was selected for enrichment culture, which was used for subsequent strain identification.

Example 2 Identification of Strains

Figure 1:
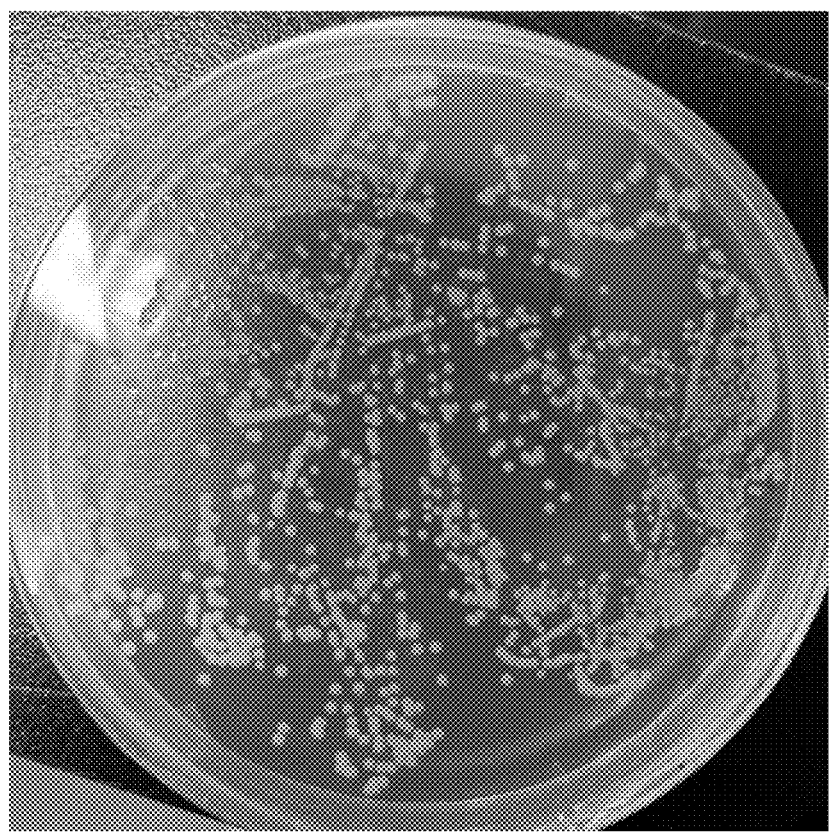
FIG. 1 is a morphological map of a single colony of *Zavarzinia compransoris* GDUTXIONG2.
Figure 2:
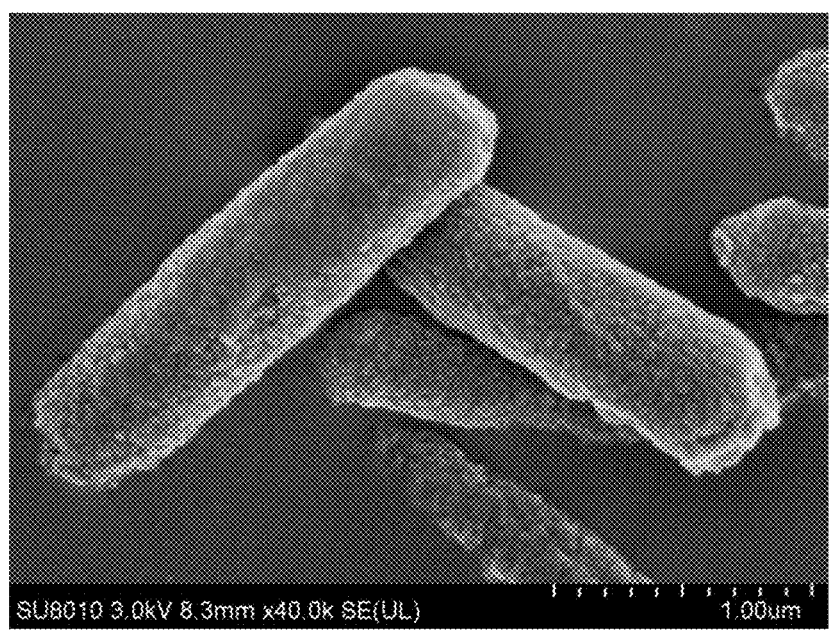
FIG. 2 is a view showing the morphology of the *Zavarzinia compransoris* GDUTXIONG2 strain under an electron scanning microscope.

The colony after enrichment culture in Example 1 was taken for strain identification, and the morphological characteristics of the colony after culture in a solid medium for 24 h were observed under an electron microscope; the colony morphology was shown in FIG. 1, which was round, off-white and translucent, with a colony diameter of 0.5-1.5 mm; the morphology of the bacteria was rod-shaped, as shown in FIG. 2, the size of the bacteria was 0.8-1.0×0.2-0.3 μm, without flagella.

Then the physiological and biochemical characteristics are identified, and the identification process is referred to *Bergey's Manual of Determinative Bacteriology*, 8th Edition. The identification results were as shown in Table 1 below:

TABLE 1

| Physiological and biochemical characteristics of bacteria | |
|---|---|
| Item | Test results |
| Gram stain | − |
| Anaerobic growth | + |
| Oxidase | + |
| Nitrate reduction | − |
| Simon's citrate utilization | − |
| Hydrolyzed gelatin (4° C. liquid) | − |
| Glucose OF utilization | + |
| Arabinose utilization | − |
| Mannitol utilization | − |
| Xylose utilization | − |

Note: The reaction status is divided into positive and negative, with the positive shape coded as "+" and the negative shape coded as "−".

Then the molecular biology identification was carried out and total bacterial DNA was extracted using a DNA extraction kit. Bacterial 16S rDNA general primers were used:

```
Forward primer:
                                         (SEQ ID NO: 1)
7F(5'-CAGAGTTTGATCCTGGCT-3')

Reverse primer:
                                         (SEQ ID NO: 2)
1540R(5'-AGGAGGTGATCCAGCCGCA-3')
```

The 16S rDNA gene was amplified, and the 16S rRNA gene sequence with a length of around 1,500 bp (SEQ ID NO: 3) was compared with the registered gene sequence in Genbank. The homology comparison results were shown in FIG. 3. The comparative analysis found that the strain isolated in the present invention was most similar to *Zavarzinia compransoris* strain Z-1155, with a similarity of 99.85%.

Based on the above morphological, physiological, and biochemical characteristics and 16S rRNA gene sequence identification results, the strain isolated in the present invention was assigned to *Zavarzinia compransoris*, named *Zavarzinia compransoris* GDUTXIONG2, and deposited in China Center for Type Culture Collection (CCTCC) on Jun.

10, 2022, with the accession number of CCTCC NO: M 2022855, deposited at No. 299, Bayi Road, Wuchang District, Wuhan, Hubei.

Example 3 Degradation of Organophosphorus Flame Retardants by Strains

The example is a study of the *Zavarzinia compransoris* GDUTXIONG2 identified in the previous example on the organophosphorus flame retardant tris (1,3-dichloropropyl) phosphate (TDCPP). First, an inorganic salt medium was prepared in a conical flask by adding 100 mL of formula components of the inorganic salt medium and autoclaved at 121° C. for 30 min for later use. After enrichment and enrichment cultivation of GDUTXIONG2 strain in a solid medium for 18 h, bacteria were collected by centrifugation and washed three times with a phosphate buffer, then suspended in the above conical flask containing 100 mL of the inorganic salt medium at 10% inoculum size, and a certain amount of TDCPP solution was added to make the concentration to be 1 mg/L, 5 mg/L, 10 mg/L and 15 mg/L, respectively, and cultivated at temperature of 37° C., vibration frequency of 200 r/min for performing degradation experiment. Samples were taken at 96 h to determine the concentration of TDCPP in the solution, and the concentration of TDCPP during degradation was determined by gas chromatography-mass spectrometry (GC-MS, Agilent, USA, 7890A-5975C).

The detection conditions of gas chromatography-mass spectrometry were: 1 μL of the sample was passed into a chromatography column DB-5MS (30 m×0.25 mm×0.25 μm, J & W Scientific, Folsom, CA, USA) in splitless mode. The initial temperature of the heating program was 60° C. to retain 1 min, 15° C./min to 150° C., then 10° C./min to 300° C. maintaining 5 min. The ion source temperature of the mass detector was 230° C. and the electron energy was 70 eV. In full scan mode, the m/z scan range is 30-1100 amu.

Figure 4:
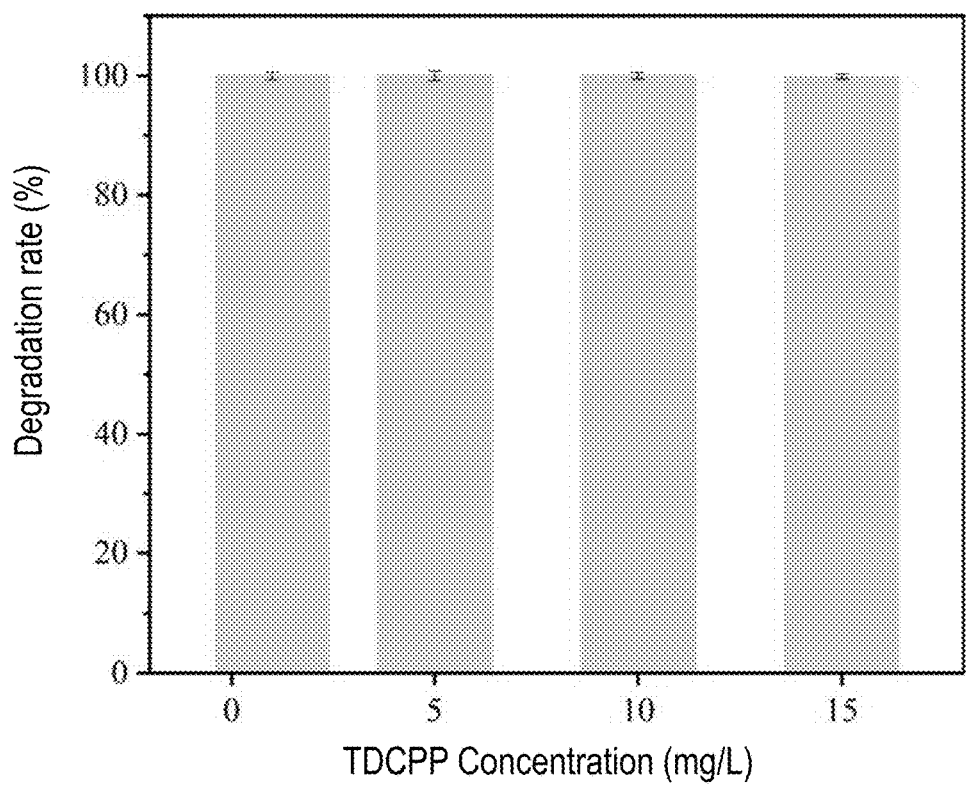
FIG. 4 is a graph of the degradation rate of *Zavarzinia compransoris* GDUTXIONG2 at different initial TDCPP concentrations.

The degradation results of GDUTXIONG2 strain to different initial concentrations of TDCPP are shown in FIG. 4 below. The results show that the degradation capacity of GDUTXIONG2 strain to TDCPP can reach more than 99.9% at 96 h; it has a good degradation effect on organophosphorus flame retardants and can be applied to the remediation of organophosphorus flame retardant contamination and the purification treatment of organophosphorus flame retardants released from electronic waste in water, sediment, and soil.

Example 4 Degradation of Organophosphorus Flame Retardant in Wastewater

The example is a study of the *Zavarzinia compransoris* GDUTXIONG2 identified in the previous example on the organophosphorus flame retardant tris (1,3-dichloropropyl) phosphate (TDCPP). After enrichment and enrichment cultivation of GDUTXIONG2 strain in a solid medium for 18 h, the bacteria were collected by centrifugation and washed with phosphate buffer three times, then suspended in an erlenmeyer flask containing 100 mL of sterilized wastewater containing TDCPP at 10% inoculum size, the TDCPP concentration of the wastewater was determined to be 100 mg/L and cultivated at a temperature of 37° C. and a vibration frequency of 200 r/min. Samples were taken to determine the TDCPP concentration in the solution at 12, 24, 48, 72, and 96 h, and the TDCPP concentration was determined using a gas chromatography-mass spectrometry (GC-MS, Agilent, USA, 7890A-5975C).

The detection conditions of gas chromatography-mass spectrometry were: 1 μL of the sample was passed into a chromatography column DB-5MS (30 m×0.25 mm×0.25 μm, J & W Scientific, Folsom, CA, USA) in splitless mode. The initial temperature of the heating program was 60° C. to retain 1 min, 15° C./min to 150° C., then 10° C./min to 300° C. maintaining 5 min. The ion source temperature of the mass detector was 230° C. and the electron energy was 70 eV. In full scan mode, the m/z scan range is 30-1100 amu.

Figure 5:
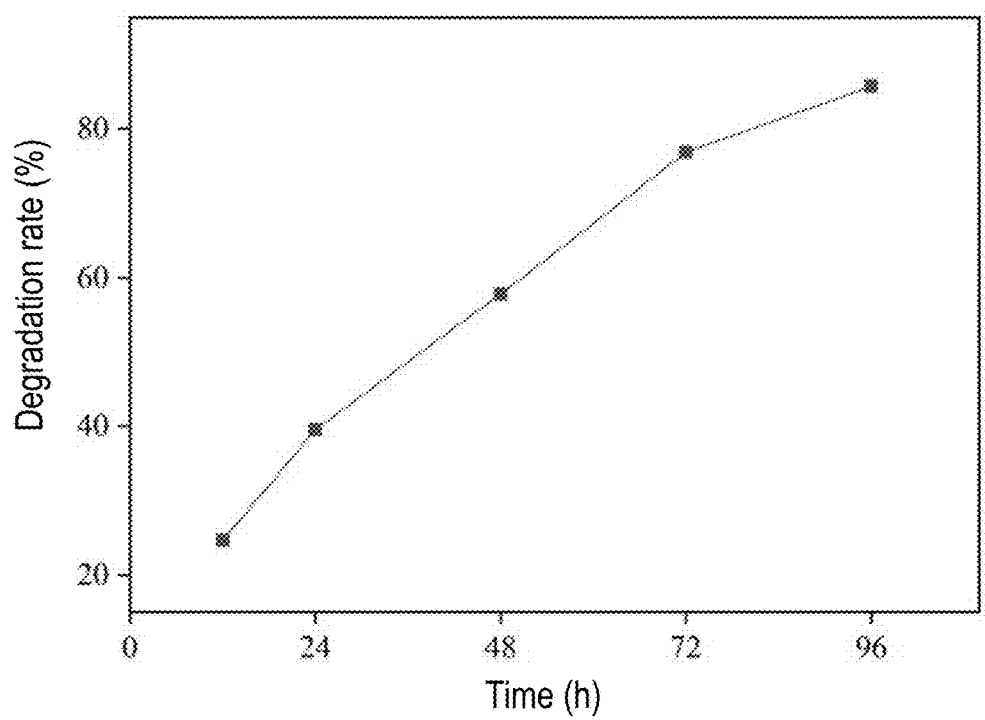
FIG. 5 is a graph of the degradation rate of TDCPP by *Zavarzinia compransoris* GDUTXIONG2 in wastewater.

The degradation results of GDUTXIONG2 strain to TDCPP in wastewater are shown in FIG. 5. The results of the example show that *Zavarzinia compransoris* GDUTXIONG2 can effectively degrade organophosphorus flame retardants in wastewater, indicating that *Zavarzinia compransoris* GDUTXIONG2 can be used in the treatment of TDCPP contamination in wastewater.

Example 5 Degradation of Organophosphorus Flame Retardants in Soil

The example is a study of the *Zavarzinia compransoris* GDUTXIONG2 identified in the previous example on the organophosphorus flame retardant tris (1,3-dichloropropyl) phosphate (TDCPP). After enrichment and enrichment cultivation of GDUTXIONG2 strain in solid medium for 18 h, the bacteria were collected by centrifugation and washed with phosphate buffer three times, then inoculated into 100 g of sterilized soil at 10% inoculum size and added with 100 mg of TDCPP, and cultivated at a temperature of 37° C. Samples were taken to determine the TDCPP concentration in the soil at 12, 24, 48, 72, and 96 h, and the TDCPP concentration was determined using a gas chromatography-mass spectrometry (GC-MS, Agilent, USA, 7890A-5975C).

The detection conditions of gas chromatography-mass spectrometry were: 1 μL of the sample was passed into a chromatography column DB-5MS (30 m×0.25 mm×0.25 μm, J & W Scientific, Folsom, CA, USA) in splitless mode. The initial temperature of the heating program was 60° C. to retain 1 min, 15° C./min to 150° C., then 10° C./min to 300° C. maintaining 5 min. The ion source temperature of the mass detector was 230° C. and the electron energy was 70 eV. In full scan mode, the m/z scan range is 30-1100 amu.

Figure 6:
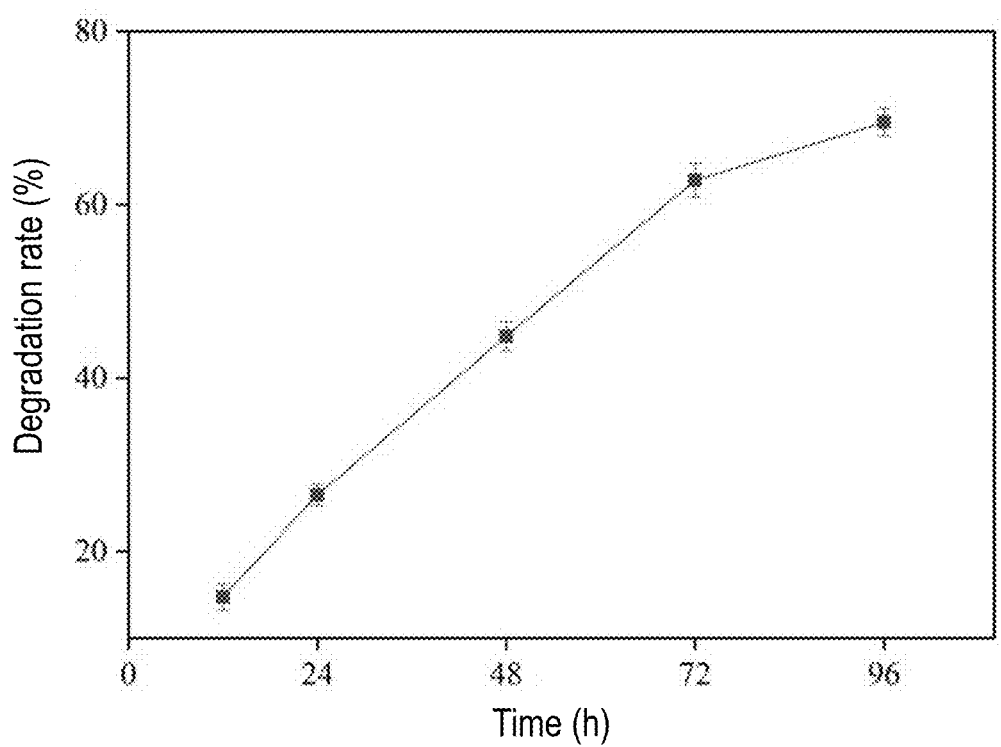
FIG. 6 is a graph of the degradation rate of TDCPP by *Zavarzinia compransoris* GDUTXIONG2 in soil.

The degradation results of GDUTXIONG2 strain to TDCPP in soil are shown in FIG. 6. The results of the example show that *Zavarzinia compransoris* GDUTXIONG2 can effectively degrade organophosphorus flame retardants in soil, indicating that *Zavarzinia compransoris* GDUTXIONG2 can be used for the treatment of TDCPP contamination in soil.

The embodiments described above are preferred embodiments of the present invention, and the embodiments of the present invention are not limited to the above embodiments, and any other changes, modifications, substitutions, combinations, and simplifications that may be made without departing from the spirit and principles of the present invention shall be equivalent replacement and shall be included in the protection scope of the present invention.

What is claimed is:

1. A *Zavarzinia compransoris* GDUTXIONG2 strain capable of degrading organophosphorus flame retardants, wherein the strain has been deposited in China Center for Type Culture Collection on Jun. 10, 2022, with the accession number CCTCC NO: M 2022855.

2. A method of use of the *Zavarzinia compransoris* GDUTXIONG2 strain of claim 1 in degradation of organophosphorus flame retardants, wherein the organophosphorus flame retardant is tris (1,3-dichloropropyl) phosphate.

3. A method of use of the *Zavarzinia compransoris* GDUTXIONG2 strain of claim 1 in preparation of a degrading microbial agent for organophosphorus flame retardants, wherein the organophosphorus flame retardant is tris (1,3-dichloropropyl) phosphate.

4. A method of use of the *Zavarzinia compransoris* GDUTXIONG2 strain of claim 1 in remediation of environments contaminated with organophosphorus flame retardants, wherein the organophosphorus flame retardant is tris (1,3-dichloropropyl) phosphate.

5. A degrading microbial agent for organophosphorus flame retardants, comprising the *Zavarzinia compransoris* GDUTXIONG2 strain of claim 1 and/or a bacterial liquid thereof.

6. The degrading microbial agent of claim 5, wherein the concentration of the bacterial liquid is not less than $2.0 \times 10^6$ CFU/mL.

7. A method for degrading organophosphorus flame retardants, wherein the organophosphorus flame retardant is treated with the *Zavarzinia compransoris* GDUTXIONG2 strain of claim 1 and/or the bacterial liquid thereof; the organophosphorus flame retardant is tris (1,3-dichloropropyl) phosphate.

8. The method of claim 7, wherein an inoculum size of the strain is 1%-10%.

9. The method of claim 7, wherein treatment conditions are: pH 6.5-7.5, temperature 30-40° C., and time 24-120 h.

* * * * *